(12) United States Patent
Vemishetti et al.

(10) Patent No.: US 7,205,402 B2
(45) Date of Patent: Apr. 17, 2007

(54) SYNTHESIS OF A BENZOXAZINONE

(75) Inventors: Purushotham Vemishetti, Monmouth Junction, NJ (US); Scott T. Chadwick, Redwood City, CA (US); Carrie A. Costello, Rensselaer, NY (US); Sridhar Desikan, Hillsborough, NJ (US); Emily A. Reiff, Milltown, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/217,892

(22) Filed: Sep. 1, 2005

(65) Prior Publication Data

US 2006/0047115 A1    Mar. 2, 2006

Related U.S. Application Data

(60) Provisional application No. 60/606,702, filed on Sep. 2, 2004.

(51) Int. Cl.
*C07D 265/18*   (2006.01)
(52) U.S. Cl. .......................... 544/92; 544/90
(58) Field of Classification Search ............ 544/92
See application file for complete search history.

(56) References Cited

U.S. PATENT DOCUMENTS 5,922,864 A * 7/1999 Frey et al. .................... 544/92

OTHER PUBLICATIONS

Pierce et al. J. Org. Chem. 1998, 63, 8536-8543.*
Pierce et al., "Practical Asymmetric Synthesis of Efavirenz (DMP 266), and HIV-1 Reverse Transcriptase Inhibitor", J. Org. Chem., vol. 63, p. 8536-8543, 1998.
Radesca et al., "Synthesis of HIV-1 Reverse Transcriptase Inhibitor DMP 266", Synthetic Communications, vol. 27(24), pp. 4373-4384, 1997.

* cited by examiner

*Primary Examiner*—Kahsay Habte
(74) *Attorney, Agent, or Firm*—Mary K. VanAtten; Jennifer Chin Chapman

(57) ABSTRACT

The present invention provides novel methods for the synthesis of (S)-6-chloro-4-cyclopropylethynyl-4-trifluoromethyl-1,4-dihydro-2H-3,1-benzoxazin-2-one of formula (III)

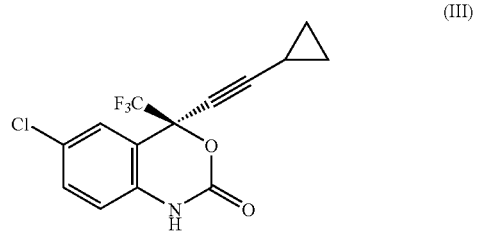

which is useful as a human immunodeficiency virus (HIV) reverse transcriptase inhibitor.

11 Claims, 2 Drawing Sheets

SYNTHESIS OF A BENZOXAZINONE

This application claims a benefit of priority from U.S. Provisional Application No. 60/606,702, filed Sep. 2, 2004, the entire disclosure of which is herein incorporated by reference.

FIELD OF THE INVENTION

The present invention provides novel methods for the synthesis of (S)-6-chloro-4-cyclopropylethynyl-4-trifluoromethyl-1,4-dihydro-2H-3,1-benzoxazin-2-one which is useful as human immunodeficiency virus (HIV) reverse transcriptase inhibitor.

BACKGROUND OF THE INVENTION

Reverse transcription is a characteristic of retrovirus replication. Viral replication requires a virally encoded reverse transcriptase to generate DNA copies of viral sequences by reverse transcription of the viral RNA genome. Reverse transcriptase, therefore, is a clinically relevant target for the chemotherapy of retroviral infections because the inhibition of virally encoded reverse transcriptase would interrupt viral replication.

A number of compounds are effective in the treatment the human immunodeficiency virus (HIV) which is the retrovirus that causes progressive destruction of the human immune system with the resultant onset of AIDS. Effective treatment through inhibition of HIV reverse transcriptase is known for both nucleoside based inhibitors, such as azidothymidine, and non-nucleoside based inhibitors. Benzoxazinones have been found to be useful non-nucleoside based inhibitors of HIV reverse transcriptase. The (S)-6-chloro-4-cyclopropylethynyl-4-trifluoromethyl-1,4-dihydro-2H-3,1-benzoxazin-2-one of formula (III):

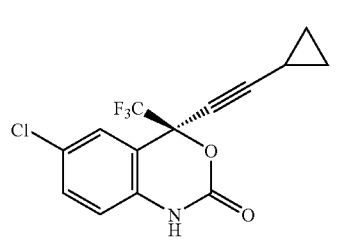

also known as efavirenz, is not only a highly potent reverse transcriptase inhibitor, it is also efficacious against HIV reverse transcriptase resistance. Due to the importance of the compound (III) as a reverse transcriptase inhibitor, economical and efficient synthetic processes for its production need to be developed.

The final step in preparing the compound (III) is the cyclization reaction from compound (I).

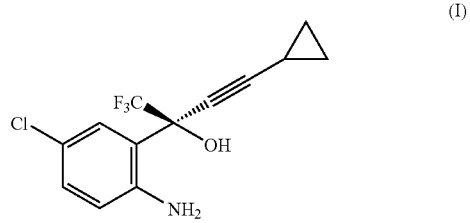

This is done commercially using phosgene to prepare efavirenz. Phosgene is a highly toxic gas and it would be advantageous to prepare the compound without the use of phosgene.

U.S. Pat. No. 5,922,864 describes a method for preparing the compound (III) by a cyclization reaction involving alkyl and aryl chloroformates. However, the method using alkyl chloroformates involves isolating the carbamate intermediate.

It would be an advantage to have a cyclization procedure using less toxic ingredients and without having to isolate another intermediate in the cyclization step.

None of the above-cited references describe the methods of the present invention for the synthesis of benzoxazinones useful as inhibitors of HIV reverse transcriptase.

SUMMARY OF THE INVENTION

The present invention concerns novel processes for the preparation of benzoxazinone compounds which are useful as HIV reverse transcriptase inhibitors. The processes provide for a novel cyclization procedure to form the benzoxazinone core. The processes of the present invention provide high yields, can be conducted on a kilogram scale, and yield stable intermediates.

There is provided by this invention a process for the preparation of a compound of formula (III):

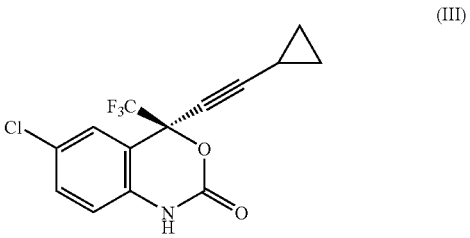

said process comprising:
(1) contacting a compound of formula (I):

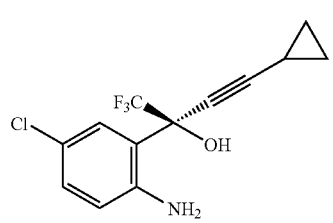

or a salt thereof; (the compound of formula (I) may exist as the MSA salt, Ia, wherein MSA is methanesulfonic acid)

with $C_{1-6}$ alkyl chloroformate in the presence of a first base, in a first solvent, at a temperature of about 20–56° C., alternatively at a temperature of about 50–56° C., under ambient atmosphere, to give a compound of formula (II)

(II):

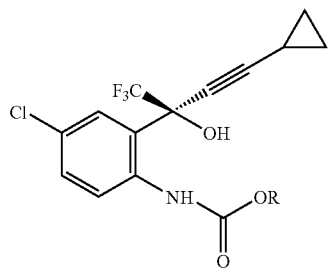

wherein R is $C_{1-6}$ alkyl;

(2) separating organic layer and concentrating to obtain the compound of formula (II) in solution;

(3) contacting the compound of formula (II) in solution with a second base at about 47–52° C. to obtain the compound of formula III.

BRIEF DESCRIPTION OF THE DRAWINGS

The invention is illustrated by reference to the accompanying drawings described below.

DETAILED DESCRIPTION OF THE INVENTION

Figure 1:
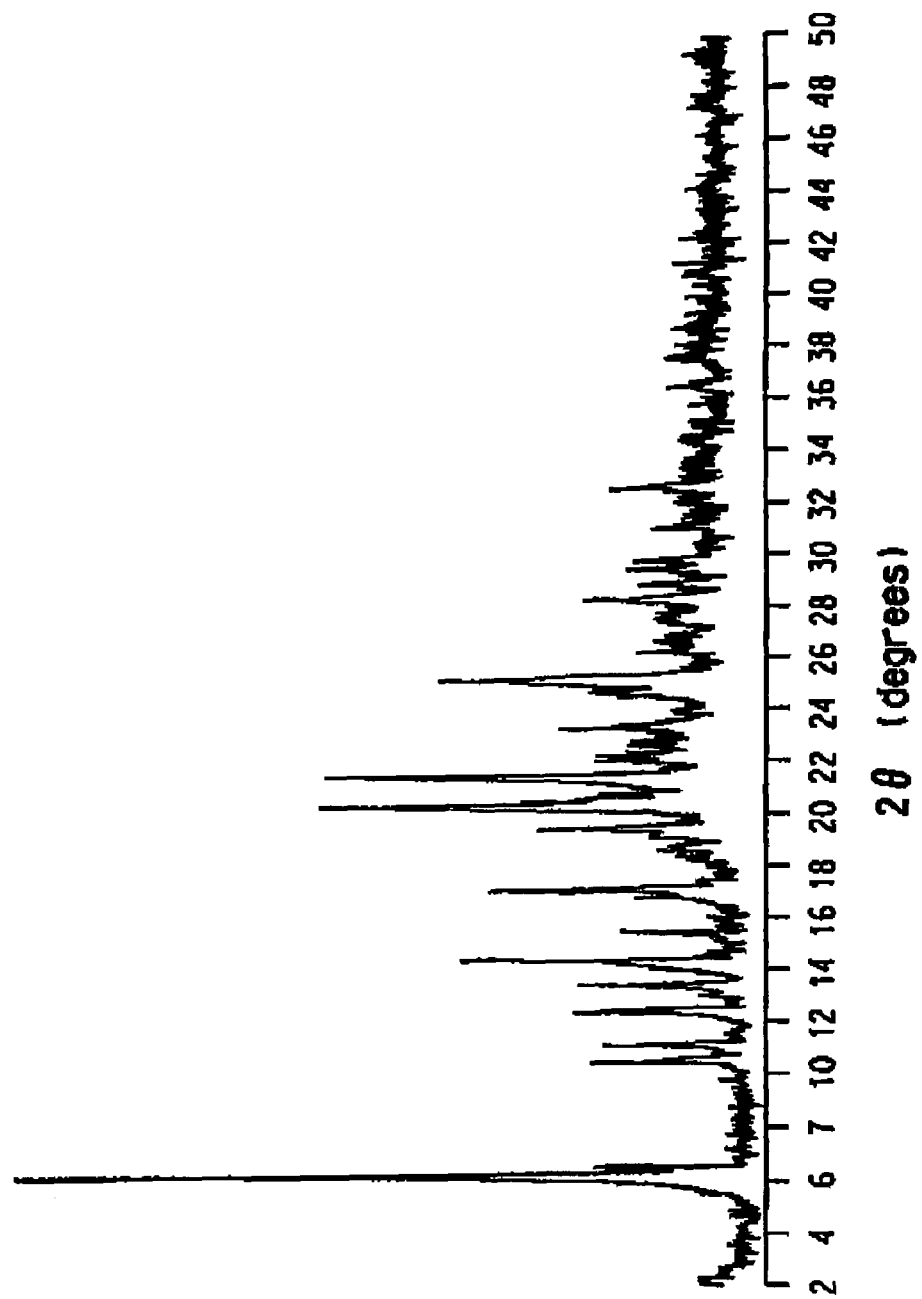
FIG. 1 shows a powder x-ray diffractogram of the Form 1 crystalline form of (S)-6-chloro-4-cyclopropylethynyl-4-trifluoromethyl-1,4-dihydro-2H-3,1-benzoxazin-2-one.

In a first embodiment, the present invention provides a novel process for the preparation of compounds of formula (III):

(III)

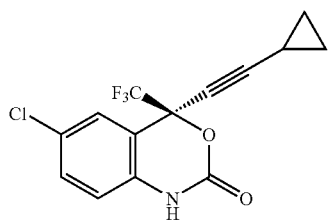

said process comprising:

(1) contacting a compound of formula (I):

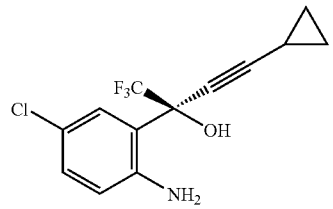

or a salt thereof;

with $C_{1-6}$ alkyl chloroformate in the presence of a first base, in a first solvent, at a temperature of about 20–56° C. (alternatively at 50–56° C.), under ambient atmosphere, to give a compound of formula (II)

(II):

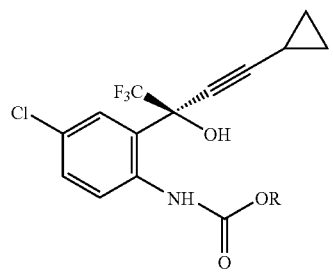

wherein R is $C_{1-6}$ alkyl;

(2) separating organic layer and concentrating to obtain the compound of formula (II) in solution;

(3) contacting the compound of formula (II) in solution with a second base at about 47–52° C. to obtain the compound of formula III.

In another embodiment the present invention provides a novel process for the preparation of compounds of formula (III), wherein the alkyl chloroformate is methyl chloroformate or ethyl chloroformate; and R is methyl or ethyl.

In another embodiment the present invention provides a novel process for the preparation of compounds of formula (III):

wherein the first base is alkali monohydrogenphosphate, alkali carbonate, alkali bicarbonate, alkali alkoxide (wherein the alkoxide is —OR and R is $C_{1-5}$ alkyl), alkali-HMDS, or alkali hydroxide, and wherein alkali is Na, K, or Li; and the first solvent is tetrahydrofuran (THF), 2-methyltetrahydrofuran (MeTHF), ethyl acetate, n-butyl acetate, isopropyl acetate, methyl t-butyl ether (MTBE), toluene, xylenes, acetonitrile, acetone, methanol, ethanol, or isopropanol.

In another embodiment the present invention provides a novel process for the preparation of compounds of formula (III):

wherein the first base is K$_2$HPO$_4$ and the second base is NaOH; and the first solvent is ethyl acetate.

In another embodiment the present invention provides a novel process for the preparation of compounds of formula (III):

wherein the solvent is ethyl acetate; and step 3 further comprises obtaining the compound of formula (III) as a solution of (III) in ethyl acetate;

washing the solution containing the compound of formula (III) with water, adding heptanes to the ethyl acetate solution and washing with aqueous HCl, water, aqueous KHCO$_3$, and water; solvent swapping the solvent and crystallizing the compound of formula (III) from heptanes-EtOAc.

In another embodiment the present invention provides a novel process for the preparation of compounds of formula (III):

wherein the crystallization of the compound of formula (III) gives Form 1 of the compound of formula (III).

In another embodiment the present invention provides a novel process for the preparation of compounds of formula (III):

wherein step 3 further comprises adding water, separating the ethyl acetate layer, concentrating the ethyl acetate layer, and adding heptanes, concentrating the solution and crystallizing the compound of formula (III).

The invention may be embodied in other specific forms without departing from the spirit or essential attributes thereof. This invention also encompasses all combinations of aspects and/or embodiments of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

The reactions of the synthetic methods claimed herein are carried out in suitable solvents which may be readily selected by one of skill in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, suitable solvents for a particular reaction step may be selected.

"Alkyl" as used herein is intended to include both branched and straight chain saturated aliphatic hydrocarbon groups having one to twelve carbon atoms. "Alkoxy" as used herein is intended to include an alkyl group of indicated number of carbon atoms attached through an oxygen bridge.

The compounds herein described may have asymmetric centers. All chiral, diastereomeric, and racemic forms are included in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

As used herein, "solvent swapping" is exchanging one primary solvent for another. This is often done by concentrating or evaporating down the solution containing the first primary solvent and adding the second solvent.

The methods of the present invention, by way of example and without limitation, may be further understood by reference to Scheme 1.

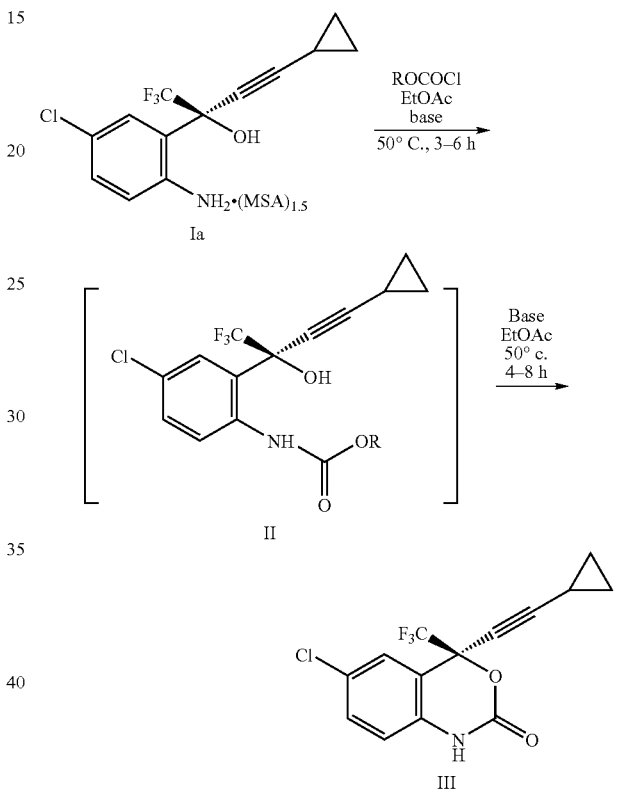

It is the object of the present invention to provide an improved process for the synthesis of benzoxazinones in multi-kilograms which are useful as HIV reverse transcriptase inhibitors.

The compound of formula (Ia) in EtOAc (ethyl acetate) was treated with ethyl chloroformate (1.15–1.20 eq) in the presence of aq (aqueous) potassium hydrogenphosphate (2.70–2.75 eq) at 55° C. for 3–6 h to furnish the ethyl carbamate (II, R=Et) solution after work up. The latter solution was treated with 50% sodium hydroxide (0.5 eq) at 50° C. for the cyclization reaction. After 4–8 h, >99% conversion to efavirenz is observed per HPLC analysis. After a series of washes and solvent exchange into heptanes having 2–5% EtOAc, crystallization afforded Form 1 efavirenz in 78–85% yield. Form 1 efavirenz could also be isolated from the propylene glycol/water crystallization method.

The polymorphic Forms (Form 1, 2, 3, 4, and 5) of efavirenz, the compound of formula (III), are described in U.S. Pat. No. 6,673,372 which is hereby incorporated by reference.

Form 1 of Efavirenz has been characterized and distinguished from other forms of Efavirenz by differential scanning calorimetry (DSC) and x-ray diffraction analysis.

In a preferred embodiment, Form 1 crystalline Efavirenz is in substantially pure form.

In another preferred embodiment, the Form 1 crystalline Efavirenz is characterized by an x-ray powder diffraction pattern comprising four or more 2θ values selected from the group consisting of 6.0±0.2, 6.3±0.2, 10.3±0.2, 10,8±0.2, 14.1±0.2, 16.8±0.2, 20.0±0.2, 20.5±0.2, 21.1±0.2, and 24.8±0.2.

In another preferred embodiment, the Form 1 crystalline Efavirenz is characterized by an x-ray powder diffraction pattern substantially in accordance with that shown in FIG. 1.

In another preferred embodiment, the Form 1 crystalline Efavirenz is characterized by a differential scanning calorimetry thermogram having a peak at about 138° C. to about 140° C.

Figure 2:
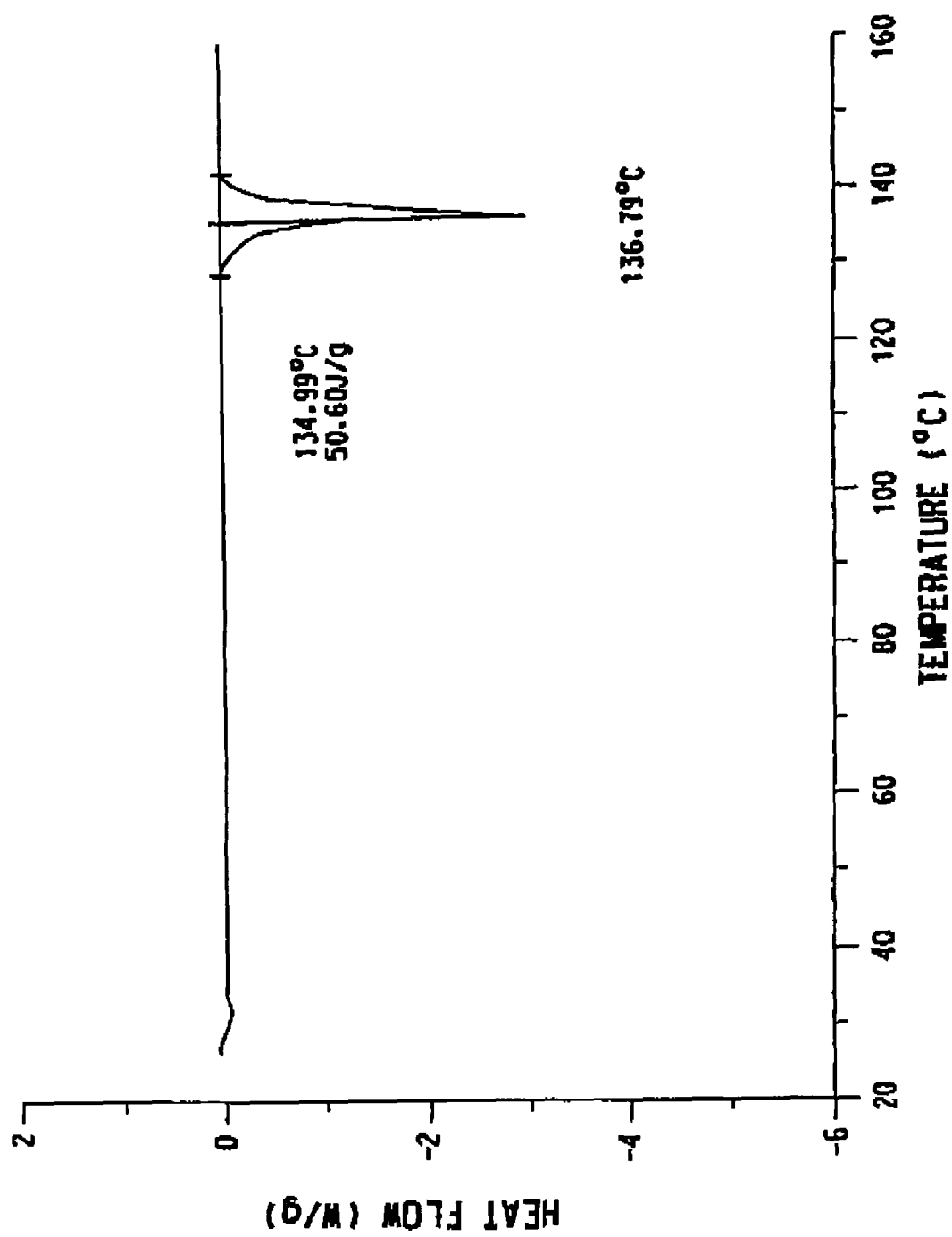
FIG. 2 shows a differential calorimetry thermogram of the Form 1 crystalline form of (S)-6-chloro-4-cyclopropylethynyl-4-trifluoromethyl-1,4-dihydro-2H-3,1-benzoxazin-2-one.

In another preferred embodiment, the Form 1 crystalline Efavirenz is characterized by a differential scanning calorimetry thermogram substantially in accordance with that shown in FIG. 2.

In a more preferred embodiment, the Form 1 crystalline Efavirenz is characterized by an x-ray powder diffraction pattern comprising four or more 2θ values selected from the group consisting of: 6.0±0.2, 6.3±0.2, 10.3±0.2, 10.8±0.2, 14.1±0.2, 16.8±0.2, 20.0±0.2, 20.5±0.2, 21.1±0.2, and 24.8±0.2, and further characterized by a differential scanning calorimetry thermogram having a peak at about 138° C. to about 140° C.

In another more preferred embodiment, the Form 1 crystalline Efavirenz is characterized by an x-ray powder diffraction pattern substantially in accordance with that shown in FIG. 1, and is further characterized by a differential scanning calorimetry thermogram having a peak at about 138° C. to about 140 ° C.

Exchanging methyl chloroformate for ethyl chloroformate in the above process gave higher yield, 89–92%, but storage of methyl chloroformate at a manufacturing site requires Process Safety Management (PSM) as per OSHA and Risk Management Process (RMP) as per EPA. Other alkyl chloroformates, R=Pr, iPr, n-Bu, iBu, t-Bu, allyl, 2-methoxyethyl, trichloroethyl and Bn, were also evaluated for the synthesis of efavirenz.

The carbamate (II) is formed using a base such as alkali monohydrogenphosphate (preferably $K_2HPO_4$), alkali carbonate, alkali bicarbonate, alkali t-butoxide, alkali alkoxide (wherein the alkoxide is —O—R wherein R is $C_{1-5}$ alkyl), alkali-HMDS (hexamethyldisilazide), or alkali hydroxide, and wherein alkali is Na, K, or Li.

Examples of other solvents that may be used in the preparation of the carbamate (II) are methyl t-butyl ether (MTBE), tetrahydrofuran (THF), 2-methylTHF (MeTHF), n-butyl acetate, isopropyl acetate, toluene, xylenes, acetonitrile, acetone, methanol, ethanol, and isopropanol.

Conversion of the carbamate (II) solution to efavirenz (III) can be accomplished equally well with anhydrous bases such as Li/K/NaHMDS, Li/K/Na—OR (R=$C_{1-5}$ alkyl) and BuLi.

It was discovered that crystallization from 2–5% EtOAc in heptanes is a rugged process to give directly Form 1 efavirenz exclusive of other forms (Form 2, 3, 4 and 5). Seeding with different forms (2, 3, 4 and 5 in place of Form 1 in the reaction process affords Form 1 exclusively. The Form 1 polymorph is desired because it is the polymorph used for formulation of drug product. All previous commercial processes required a thermal process (at 85–95° C.) to convert from Form 4 to Form 1.

Experimental Procedures

Procedure 1:

Preparation of Efavirenz (the Compound III) Using aq NaOH as the Second Base

To a 25 L glass reactor equipped with mechanical agitator, thermocouple and addition funnel, compound Ia (1 kg, 2.31 mol), EtOAc (5 L) and aq $K_2HPO_4$ (prepared from 1.084 Kg $K_2HPO_4$ in 5 L water) were added sequentially at 25° C. Ethyl chloroformate (0.261 L, 2.65 mol) was added over 5 min at 25° C., and the resulting biphasic mixture was heated to 50° C. After 3–6 h of agitation, formation of II was complete as per HPLC. The reaction mixture was cooled to room temperature and the water layer was separated from the organic phase. The latter phase was washed with water and azeotropically distilled to give rich ethyl carbamate solution (II, R=Et) (10 L).

50% sodium hydroxide (0.092 Kg, 1.15 mol) was added to rich ethyl carbamate solution (II, R=Et, 10 L) and stirred at 50° C. for 4–8 h for the cyclization reaction. After the reaction mixture was cooled to room temperature, the organic phase was washed with water (5 L). The rich efavirenz solution was diluted with an equal volume of heptanes (10 L) and washed with 9M HCl (5 L) at 0–5° C. followed by subsequent washes with water (5 L), aq 10% $KHCO_3$ (5 L) solution and water (5 L) at room temperature. Rich efavirenz solution was co-distilled under vacuum with heptanes to get the desired EtOAc range (2.5–5.0%; 13–15 L/Kg). It was heated to 65° C. to form a clear solution, which was cooled to 45–50° C., seeded with Form 1 efavirenz (5 g) and held at 45–50° C. to form an opaque slurry in 1–2 h. The crystal slurry was cooled to 20–25° C. over 2–4 h and to −8 to −12° C. over 2 h. After 2 h of holding period at −8 to −12° C., the slurry was filtered. The cake was washed with cold heptanes (−8 to −12° C., 4–6 L) and dried at <50° C. under vacuum to give efavirenz as Form 1, 78–85% yield, 0.56–0.62 Kg.

Procedure 2:

Preparation of Efavirenz Using Solid NaOH as the Second Base

Compound Ia (50.0 g, 115 mmol, 1.00 equiv) was slurried in ethyl acetate (3–5 mL/g). Aqueous potassium phosphate dibasic (55.2 g, 317 mmol, 2.75 equiv in 5 mL/g water) was freshly prepared and charged to the slurry followed by ECF (ethyl chloroformate) (13.6 mL, 143 mmol, 1.15–1.20 equiv, corrected for potency). The biphasic reaction mixture was warmed to 55° C. and was complete in 2 hours. After the phase split and water wash (5 mL/g), the % water in the carbamate solution was reduced by azeotropic distillation. The carbamate solution in ethyl acetate (5–10 mL/g) was cyclized using solid NaOH (2.32 g, 57.6 mmol, 0.500 equiv) at 50° C. giving 0.46 AP II (R=Et) after 4 hours with compound I levels at 0.49 AP. The batch was washed with water (5 mL/g) twice, distilled to ~2–3 mL/g, heptanes were added and the solvent swap was completed giving 3% ethyl acetate. After heating at 60–65° C. to obtain a homogeneous solution, the batch was cooled to 47° C. and seeded with Form 1 of compound III. The resulting slurry was held at 45° C. for 2.5 hours and cooled to 25° C. over two hours. The batch was cooled to −10° C. over one hour and held two hours. The slurry was filtered and washed with cold heptanes (2×2 mL/g). The wet cake was dried at 50° C. giving compound III (32.8 g, 90.1 M % yield).

Procedure 3:

Preparation of Efavirenz from (I) (Using Anhydrous Base For Cyclization)

Addition of 1.1 eq of anhydrous base (such as LiOtBu, NaOtBu, KOtBu, LiHMDS, KHMDS, NaHMDS, BuLi) in place of 50% sodium hydroxide in the above cyclization reaction of compound (II) solution, furnished a 100% conversion to Efavirenz in 4–6 h at 50–70° C. The reaction mixture was quenched with 1.0 N AcOH to neutral pH and washed with water. The resulting rich efavirenz solution was exchanged into heptanes/2.5–5% EtOAc (13 L/Kg) and crystallized as described above to give efavirenz as Form 1 in 86–89% yield.

Procedure 4:

Isolation of Form 1 Efavirenz in the Presence of Other Form Seeds from EtOAc/heptanes A solution of efavirenz at 15 ml/g (2.23% ethyl acetate in heptanes) and at 65° C. was transferred via cannula to four reaction flasks in 75 ml aliquots. The solutions were seeded near 50° C. and also near 25° C. (actual temperatures in parentheses) with Form 2 (59° C., 28° C.), Form 3 (53° C., 25° C.), and Form 4 (50° C., 25° C.) Form 5 (45° C., 25° C.), efavirenz, respectively. All seed amounts were 25 mg. The slurries were cooled to −5° C., filtered, washed with cold heptanes, and dried at 50° C. Samples were taken for Form at 32° C., room temperature, −5° C., and dry cake. The samples at all temperatures for Form 2, Form 3, and Form 4 seeding were Form 1 only by PXRD (XRPD), for a description of the XRPD, see U.S. Pat. No. 6,673,372.

Although the present invention has been described with respect to specific embodiments, the details of these embodiments are not to be construed as limitations. Various equivalents, changes and modification may be made without departing from the spirit and the scope of this invention, and it is understood that such equivalent embodiments are part of this invention. The present invention may be embodied in other specific forms without departing from the spirit or essential attributes thereof and, accordingly, reference should be made to the appended claims as further indicating the scope of the invention.

What is claimed is:

1. A process for the synthesis of a compound of formula (III):

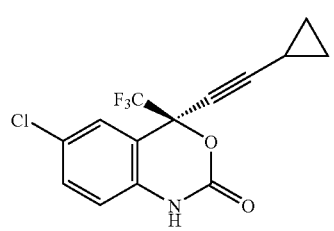

said process comprising:

(1) contacting a compound of formula (I):

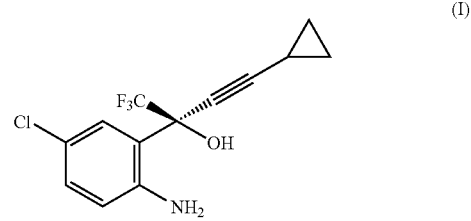

or a salt thereof, with $C_{1-6}$ alkyl chloroformate in the presence of a first base, in a solvent, at a temperature of about 20–56° C., under ambient atmosphere, to give a compound of formula (II)

(II):

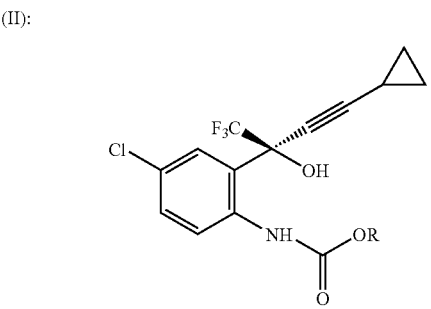

wherein R is $C_{1-6}$ alkyl;

wherein the first base is $K_2HPO_4$;

wherein the solvent is selected from the group consisting of THF, MeTHF, ethyl acetate, n-butyl acetate, isopropyl acetate, methyl t-butyl ether (MTBE), toluene, xylenes, acetonitrile, acetone, methanol, ethanol, and isopropanol;

(2) separating organic layer and concentrating to obtain the compound of formula (II) in solution; and (3) contacting the compound of formula (II) in solution with a second base NaOH at about 47–52° C. to obtain the compound of formula III.

2. A process according to claim 1 wherein: the alkyl chloroformate is methyl chloroformate or ethyl chloroformate.

3. A process according to claim 1 wherein: the solvent is ethyl acetate.

4. The process according to claim 1 which further comprises the step (4) obtaining the compound of formula (III) as a solution of (III) in ethyl acetate; washing the solution containing the compound of formula (III) with water, adding heptane(s) to the ethyl acetate solution and washing with aqueous HCl, water, aqueous $KHCO_3$, and water again; distilling the solvent and crystallizing the compound of formula (III) from heptanes-EtOAc.

5. The process according to claim 4 wherein the crystallization of the compound of formula (III) gives Form 1 of the compound of formula (III).

6. A process for the synthesis a compound of formula (III):

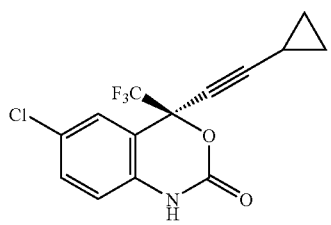

said process comprising:

(1) contacting a compound of formula (I):

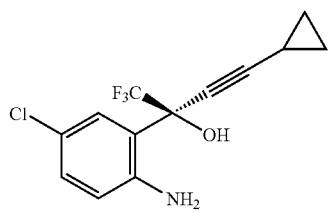

or a salt thereof, with C$_{1-6}$ alkyl chloroformate in the presence of a first base, in a solvent, at a temperature of about 20–56° C., under ambient atmosphere, to give a compound of formula (II)

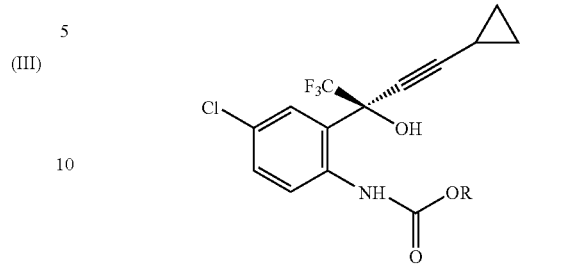

wherein R is C$_{1-6}$ alkyl;
wherein the first base is K$_2$HPO$_4$;
wherein the solvent is ethyl acetate;
  (2) separating organic layer and concentrating to obtain the compound of formula (II) in solution; and
  (3) contacting the compound of formula (II) in solution with a second base NaOH at about 47–52° C. to obtain the compound of formula III.

7. The process according to claim 6 which further comprises the step of:
  (4) adding water, separating the ethyl acetate layer, concentrating the ethyl acetate, adding heptanes, concentrating the solution and crystallizing the compound of formula (III).

8. The process according to claim 6 wherein:
the alkyl chloroformate is methyl chloroformate or ethyl chloroformate.

9. The process according to claim 7 wherein:
the crystallization of the compound of formula (III) gives Form 1 of the compound of formula (III).

10. The process according to claim 1, wherein the compound of formula (III) is Form 1.

11. The process according to claim 6, wherein the compound of formula (III) is Form 1.

* * * * *